United States Patent [19]
Stern et al.

[11] Patent Number: 6,086,918
[45] Date of Patent: *Jul. 11, 2000

[54] ORAL PEPTIDE PHARMACEUTICAL PRODUCTS

[75] Inventors: William Stern, Tenafly; James P. Gilligan, Union, both of N.J.

[73] Assignee: Unigene Laboratories, Inc., Fairfield, N.J.

[ * ] Notice: This patent is subject to a terminal disclaimer.

[21] Appl. No.: 09/125,500

[22] PCT Filed: Mar. 14, 1997

[86] PCT No.: PCT/US97/04024

§ 371 Date: Aug. 19, 1998

§ 102(e) Date: Aug. 19, 1998

[87] PCT Pub. No.: WO97/33531

PCT Pub. Date: Sep. 18, 1997

Related U.S. Application Data

[63] Continuation-in-part of application No. 08/616,250, Mar. 15, 1996, Pat. No. 5,912,014.

[51] Int. Cl.[7] .................. A61K 9/28; A61K 9/30
[52] U.S. Cl. ............ 424/474; 424/475; 424/477; 424/480; 424/491; 424/457; 424/459; 424/461; 424/426; 514/3; 514/808; 514/807
[58] Field of Search .................. 424/474, 475, 424/477, 480, 491, 457, 459, 461, 426; 514/3, 808, 807

[56] References Cited

U.S. PATENT DOCUMENTS

| | | |
|---|---|---|
| 4,604,376 | 8/1986 | Teng . |
| 4,708,934 | 11/1987 | Gilligan . |
| 4,994,439 | 2/1991 | Longenecker et al. . |
| 5,122,376 | 6/1992 | Aliverti et al. . |
| 5,206,219 | 4/1993 | Desai .......................................... 514/3 |
| 5,310,727 | 5/1994 | Lattanzi et al. . |
| 5,350,741 | 9/1994 | Takada ........................................ 514/3 |
| 5,447,729 | 9/1995 | Belenduik et al. . |
| 5,472,710 | 12/1995 | Klokkers-Bethke et al. .......... 424/468 |

FOREIGN PATENT DOCUMENTS

| | | |
|---|---|---|
| 0308067 | 8/1988 | European Pat. Off. . |
| 0382403 | 2/1990 | European Pat. Off. . |
| 0517211 | 6/1992 | European Pat. Off. . |
| 9528963 | 4/1994 | WIPO . |

OTHER PUBLICATIONS

Rico, et al., *Current Therapeutic Research*, vol. 49, No. 1, Abstract (1991).
Aungst, *J. Pharma. Sci.*, 82(10):979–987 (1993).
Lang, et al., *Am. J. Physiol.*, 251(3 Pt 1):341–8 (1986).
Fix, et al., *Am. J. Physiol.*, 251(3 Pt 1):332–40 (1986).
Ohwaki, et al., *J. Pharm. Sci.*, 76(9):695–99 (1987).
Langguth, et al., *Pharm. Research*, 11(4):528 (1994).
Ray, et al., *Biotechnology*, 11:64–70 (1993).
Kagatani, et al., *Pharmaceutical Research*, 13(5):739–743 (1996).
Rico, et al., *Current Therapeutic Research*, 49(1):31–37 (1991).
Vector Pharma Ongoing Research "Oral Delivery of Peptides" no date, no source.

*Primary Examiner*—Ali Salimi
*Attorney, Agent, or Firm*—Ostrolenk, Faber, Gerb & Soffen, LLP

[57] ABSTRACT

Bioavailability of peptide active agents to be administered orally is enhanced by a pharmaceutical composition providing targeted release of the peptide to the intestine by virtue of an acid-resistant protective vehicle which transports components of the invention through the stomach. The composition includes an absorption enhancer and a sufficient amount of a pH-lowering agent to lower local intestinal pH. All components are released together into the intestine with the peptide.

55 Claims, No Drawings

ORAL PEPTIDE PHARMACEUTICAL PRODUCTS

RELATED APPLICATIONS

This application is a 35 U.S.C. § 371 national phase conversion of International Application PCT/US97/04024 filed Mar. 14, 1997 which is, in turn, a continuation in part of U.S. application Ser. No. 08/616,250 filed Mar. 15, 1996, now U.S. Pat. No. 5,912,014. Priority of all of the foregoing applications is claimed.

BACKGROUND OF THE INVENTION

1. Field of the Invention

The present invention relates to oral peptide pharmaceuticals where the active compounds include a plurality of amino acids and at least one peptide bond in their molecular structures, and to methods of enhancing bioavailability of such peptide active compounds when administered orally.

2. Description of the Related Art

Numerous human hormones, neurotransmitters and other important biological compounds have peptides as a substantial part of their molecular structures. Many diseases respond positively to raising the level of these peptide compounds in patients. Therapeutically effective amount of such biologically relevant peptides may be administered to patients in a variety of ways. However, as discussed further below, preferred oral administration is very difficult with this type of active compound.

Salmon calcitonin, for example, is a peptide hormone which decreases uptake of calcium from bone. When used to treat bone-related diseases and calcium disorders (such as osteoporosis, Paget's disease, hypercalcemia of malignancy, and the like), it has the effect of helping maintain bone density. Many types of calcitonin have been isolated (human calcitonin, salmon calcitonin, eel calcitonin, elkatonin, porcine calcitonin, and chicken calcitonin). There is significant structural non-homology among the various calcitonin types. For example, there is only 50% percent identity between the amino acids making up human calcitonin and those making up salmon calcitonin. Notwithstanding the difference in molecular structure, salmon calcitonin may be used in the human treatment of the calcitonin-responsive diseases discussed above.

Peptide pharmaceuticals used in the prior art frequently have been administered by injection or by nasal administration. Insulin is one example of a peptide pharmaceutical frequently administered by injection. A more preferred oral administration tends to be problematic because peptide active compounds are very susceptible to degradation in the stomach and intestines. For example, the prior art is not believed to have reported an ability to achieve reproducible blood levels of salmon calcitonin when administered orally. This is believed to be because salmon calcitonin lacks sufficient stability in the gastrointestinal tract, and tends to be poorly transported through intestinal walls into the blood. However, injection and nasal administration are significantly less convenient than, and involve more patient discomfort than, oral administration. Often this inconvenience or discomfort results in substantial patient noncompliance with a treatment regimen. Thus, there is a need in the art for more effective and reproducible oral administration of peptide pharmaceuticals like insulin, salmon calcitonin and others discussed in more detail herein.

Proteolytic enzymes of both the stomach and intestines may degrade peptides, rendering them inactive before they can be absorbed into the bloodstream. Any amount of peptide that survives proteolytic degradation by proteases of the stomach (typically having acidic pH optima) is later confronted with proteases of the small intestine and enzymes secreted by the pancreas (typically having neutral to basic pH optima). Specific difficulties arising from the oral administration of a peptide like salmon calcitonin involve the relatively large size of the molecule, and the charge distribution it carries. This may make it more difficult for salmon calcitonin to penetrate the mucus along intestinal walls or to cross the intestinal brush border membrane into the blood. These additional problems may further contribute to limited bioavailability.

SUMMARY OF THE INVENTION

It is accordingly an object of the present invention to provide a therapeutically effective oral pharmaceutical composition for reliably delivering pharmaceutical peptides, e.g., physiologically active peptide agents such as insulin, salmon calcitonin, vasopressin and others discussed herein.

It is a further object of the invention to provide therapeutic methods for enhancing the bioavailability of such peptides.

It is a further object of the invention to provide methods of treating bone-related diseases and calcium disorders by administering salmon calcitonin orally.

In one aspect, the invention provides a pharmaceutical composition for oral delivery of a physiologically active peptide agent comprising:

(A) a therapeutically effective amount of said active peptide agent;

(B) at least one pharmaceutically acceptable pH-lowering agent;

(C) at least one absorption enhancer effective to promote bioavailability of said active agent; and (D) an acid resistant protective vehicle effective to transport said pharmaceutical composition through the stomach of a patient while preventing contact between said active peptide agent and stomach proteases;

wherein said pH-lowering agent is present in said pharmaceutical composition in a quantity which, if said composition were added to ten milliliters of 0.1M aqueous sodium bicarbonate solution, would be sufficient to lower the pH of said solution to no higher than 5.5.

Preferred peptide active agents include but are not limited to insulin, vasopressin salmon calcitonin and others discussed below, especially salmon calcitonin.

In another aspect, the invention provides a method for enhancing the bioavailability of a therapeutic peptide active agent delivered orally, said method comprising selectively releasing said peptide active agent, together with at least one pH-lowering agent and at least one absorption enhancer, into a patient's intestine following passage of said peptide active agent, pH-lowering agent and absorption enhancer through said patient's mouth and stomach under protection of an acid-resistant protective vehicle which substantially prevents contact between stomach proteases and said peptide agent.

wherein said pH-lowering agent and other compounds released therewith are released into said intestine in a quantity which, if added to 10 milliliters of 0.1M aqueous sodium bicarbonate solution, would be sufficient to lower pH of said solution to no higher than 5.5.

In another aspect, the invention provides a method for enhancing the bioavailability of salmon calcitonin delivered orally, said method comprising selectively releasing said salmon calcitonin, together with at least one pH-lowering agent and at least one absorption enhancer, into a patient's intestine following passage of said salmon calcitonin, said pH-lowering agent, and said absorption enhancer through the patient's mouth and stomach under protection of an enteric coating which substantially prevents contact between stomach proteases and said salmon calcitonin;

wherein said pH-lowering compound is released by said vehicle into said intestine in an amount which, if added to 10 milliliters of 0.1M aqueous sodium bicarbonate solution, would be sufficient to lower pH of said solution to no higher than 5.5.

The present invention is believed to reduce the likelihood of proteolytic degradation of the peptide active compound by simultaneously protecting the peptide from proteolytic attack by (1) stomach proteases which are typically most active at acidic pH) and (2) intestinal or pancreatic proteases (which are typically most active at basic to neutral pH).

Then the invention is believed to promote the process by which the peptide crosses the intestinal brush border membrane into the blood, while continuing to protect the peptide from proteolytic degradation.

An acid resistant protective vehicle protects the peptide active agent from the acid-acting proteases of the stomach. Significant quantities of acid (with which the peptide active agent is intermixed) then reduce the activity of neutral to basic-acting proteases in the intestine (e.g. luminal or digestive protease and proteases of the brush border membrane) by lowering pH below the optimal activity range of these intestinal proteases. Absorption enhancers of the invention may be used to enhance transport of the peptide agent through intestinal mucous layers, through the brush border membrane and into the blood.

The simultaneous use of absorption enhancers together with a pH lowering compound, in accordance with the invention, provides a surprisingly synergistic effect on bioavailability relative to absorption enhancer alone, or pH lowering compound alone. Compare Table 4 (infra), formulation I (salmon calcitonin alone), Table 3, formulation I (salmon calcitonin and pH-lowering compound) and Table 4, formulation II (salmon calcitonin and absorption enhancer) with Table 4 formulation III (salmon calcitonin, pH-lowering compound, and absorption enhancer).

Other features and advantages of the present invention will become apparent from the following detailed description of the invention.

DETAILED DESCRIPTION OF THE INVENTION

In accordance with the invention, patients in need of treatment with peptide active ingredients are provided with an oral pharmaceutical composition thereof (at appropriate dosage), preferably but not necessarily in tablet or capsule form of an ordinary size in the pharmaceutical industry. The dosages and frequency of administering the products are discussed in more detail below. Patients who may benefit are any who suffer from disorders that respond favorably to increased levels of a peptide-containing compound. For example, oral salmon calcitonin in accordance with the invention may be used to treat patients who suffer from calcium disorders or bone diseases. The invention may be used, for example, to treat osteoporosis, Paget's disease, hypercalcemia of malignancy and the like, with oral calcitonin, preferably salmon calcitonin.

Salmon calcitonin is a preferred active ingredient for use in accordance with the invention for a number of reasons. For example, it provides a number of advantages over even human calcitonin, even though used as a pharmaceutical agent for human patients. Among the advantages provided by utilizing salmon calcitonin instead of human calcitonin for the treatment of human osteoporosis are increased potency, analgesia and increased half-life. Salmon calcitonin is more effective than natural human calcitonin in treatment, since lower dosages are necessary than with human calcitonin. There is substantial non-homology between salmon and human calcitonin, with only 50% identity in the amino acid sequences of the two calcitonins.

Applicants have found that salmon calcitonin enjoys an unexpectedly higher bioavailability when administered orally in accordance with the present invention than would be expected for its molecular weight. Applicants have discovered that, in an oral formulation of the invention, the bioavailability of salmon calcitonin significantly exceeds that of parathyroid hormone, a peptide of comparable molecular weight (34 amino acids for PTH versus 32 for sCT) in applicant's internal comparative tests.

Without intending to be bound by theory, the pharmaceutical composition of the invention is believed to overcome a series of different and unrelated natural barriers to bioavailability. Various components of the pharmaceutical compositions act to overcome different barriers by mechanisms appropriate to each, and result in synergistic effects on the bioavailability of a peptide active ingredient. As discussed below, inherent physical and chemical properties of salmon calcitonin and other peptides make certain absorption enhancers more effective than others in boosting its bioavailability.

The peptide active compound may be administered orally. In accordance with the invention, proteolytic degradation of the peptide by stomach proteases (most of which are active in the acid pH range) and intestinal or pancreatic proteases (most of which are active in the neutral to basic pH range) is reduced. Solubility enhancers aid passage of the peptide active agent through the intestinal epithelial barrier.

Again, without intending to be bound by theory, it appears that, in accordance with the present invention, the peptide is transported through the stomach under the protection of an appropriate acid-resistant protective vehicle for substantially preventing contact between the salmon calcitonin or other active peptide and any stomach proteases capable of degrading it. Once the pharmaceutical composition of the invention passes through the stomach and enters the intestinal region where basic to neutral pH predominates, and where proteases tend to have basic to neutral pH optima, the enteric coating or other vehicle releases the peptide and acid (in close proximity to each other).

The acid is believed to lower the local intestinal pH (where the active agent has been released) to levels below the optimal range for many intestinal proteases. This decrease in pH reduces the proteolytic activity of the intestinal proteases, thus affording protection to the peptide from potential degradation. The activity of these proteases is diminished by the temporarily acidic environment provided by the invention. It is preferred that sufficient acid be provided that local intestinal pH is lowered temporarily to 5.5 or below, preferably 4.7 or below and more preferably 3.5 or below. The sodium bicarbonate test described below (in the section captioned "the pH-Lowering Agent") is indicative of the required acid amount. Preferably, conditions of reduced intestinal pH persist for a time period sufficient to protect the peptide agent from proteolytic degradation until at least some of the peptide agent has had an opportunity to cross the intestinal wall into the bloodstream. For salmon calcitonin, experiments have demonstrated $T_{max}$ of 5–15 minutes for blood levels of salmon calcitonin when the active components are injected directly into the duodenum, ilium or colon. The absorption enhancers of the invention synergistically promote peptide absorption into the blood while conditions of reduced proteolytic activity prevail.

The mechanism by which the invention is believed to accomplish the goal of enhanced bioavailability is aided by having active components of the pharmaceutical composition released together as simultaneously as possible. To this end, it is preferred to keep the volume of enteric coating as low as possible consistent with providing protection from stomach proteases. Thus enteric coating is less likely to interfere with peptide release, or with the release of other components in close time proximity with the peptide. The enteric coating should normally add less than 30% to the weight of the remainder of pharmaceutical composition (i.e., the other components of the composition excluding enteric coating). Preferably, it is less than 20% and, more preferably, the enteric coating adds between 10% and 20% to the weight of the uncoated ingredients.

The absorption enhancer which may be a solubility enhancer and/or transport enhancer (as described in more detail below) aids transport of the peptide agent from the intestine to the blood, and may promote the process so that it better occurs during the time period of reduced intestinal pH and reduced intestinal proteolytic activity. Many surface active agents may act as both solubility enhancers and transport (uptake) enhancers. Again without intending to be bound by theory, it is believed that enhancing solubility provides (1) a more simultaneous release of the active components of the invention into the aqueous portion of the intestine, (2) better solubility of the peptide in, and transport through, a mucous layer along the intestinal walls. Once the peptide active ingredient reaches the intestinal walls, an uptake enhancer provides better transport through the brush border membrane of the intestine into the blood, via either transcellular or paracellular transport. As discussed in more detail below, many preferred compounds may provide both functions. In those instances, preferred embodiments utilizing both of these functions may do so by adding only one additional compound to the pharmaceutical composition. In other embodiments, separate absorption enhancers may provide the two functions separately.

Each of the preferred ingredients of the pharmaceutical composition of the invention is separately discussed below. Combinations of multiple pH-lowering agents, or multiple enhancers can be used as well as using just a single pH-lowering agent and/or single enhancer. Some preferred combinations are also discussed below.

Peptide Active Ingredients

Peptide active ingredients which may benefit from oral delivery in accordance with the invention include any therapeutic agent that is physiologically active and has a plurality of amino acids and at least one peptide bond in its molecular structure. The invention, by several mechanisms, suppresses the degradation of the active ingredients by protease that would otherwise tend to cleave one or more of the peptide bonds of the active ingredient. The molecular structure may further include other substituents or modifications. For example, salmon calcitonin, a preferred peptide active agent herein, is amidated at its C-terminus. Both man-made and natural peptides can be orally delivered in accordance with the invention.

Peptide active compounds of the invention include, but are not limited to, insulin, vasopressin, calcitonin (including not only the preferred salmon calcitonin, but other calcitonins as well). Other examples include calcitonin gene-related peptide, parathyroid hormone, luteinizing hormone-releasing factor, erythropoietin, tissue plasminogen activators, human growth hormone, adrenocorticototropin, various interleukins, enkephalin, and the like. Many others are known in the art. It is expected that any pharmaceutical compound having peptide bonds which would be subject to cleavage in the gastrointestinal tract would benefit from oral delivery in accordance with the present invention because of the reduction in such cleavage that is afforded by the present invention.

When salmon calcitonin is used, it preferably comprises from 0.02 to 0.2 percent by weight relative to the total weight of the overall pharmaceutical composition (exclusive of enteric coating) Salmon calcitonin is commercially available (for example, from BACHEM, Torrence, Calif.). Alternatively it may be synthesized by known methods, some of which are discussed briefly below. Other peptide active agents should be present at higher or lower concentrations depending on desired target blood concentrations for the active compound and its bioavailability in the oral delivery system of the invention (several are reported in Table 8).

Salmon calcitonin precursors may be made by either chemical or recombinant syntheses known in the art. Precursors of other amidated peptide active agents may be made in like manner. Recombinant production is believed significantly more cost effective. Precursors are converted to active salmon calcitonin by amidation reactions that are also known in the art. For example, enzymatic amidation is described in U.S. Pat. No. 4,708,934 and European Patent Publications 0 308 067 and 0 382 403. Recombinant production is preferred for both the precursor and the enzyme that catalyzes the conversion of the precursor to salmon calcitonin. Such recombinant production is discussed in *Biotechnology*, Vol. 11 (1993) pp. 64–70, which further describes a conversion of a precursor to an amidated product. The recombinant product reported there is identical to natural salmon calcitonin, and to salmon calcitonin produced using solution and solid phase chemical peptide synthesis.

The production of the preferred recombinant salmon calcitonin (rsCT) may proceed, for example, by producing glycine-extended salmon calcitonin precursor in *E. coli* as a soluble fusion protein with glutathione-S-transferase. The glycine-extended precursor has a molecular structure that is identical to active salmon calcitonin except at the C-terminal (where salmon calcitonin terminates -pro-$NH_2$, while the precursor terminates -pro-gly. An α-amidating enzyme described in the publications above catalyzes conversion of precursors to salmon calcitonin. That enzyme is preferably recombinantly produced, for example, in Chinese Hamster Ovary (CHO) cells) as described in the Biotechnology article cited above. Other precursors to other amidated peptides may be produced in like manner. Peptides that do not require amidation or other additional functionalities may also be produced in like manner. Other peptide active agents are commercially available or may be produced by techniques known in the art.

The pH-Lowering Agent

The total amount of the pH-lowering compound to be administered with each administration of salmon calcitonin should preferably be an amount which, when it is released into the intestine, is sufficient to lower the local intestinal pH substantially below the pH optima for proteases found there. The quantity required will necessarily vary with several factors including the type of pH-lowering agent used (discussed below) and the equivalents of protons provided by a given pH-lowering agent. In practice, the amount required to provide good bioavailability is an amount which, when added to a solution of 10 milliliters of 0.1 M sodium bicarbonate, lowers the pH of that sodium bicarbonate solution to no higher than 5.5, and preferably no higher than 4.7, most preferably no higher than 3.5. Enough acid to lower pH, in the foregoing test, to about 2.8 may been used in some embodiments. Preferably at least 300 milligrams, and more preferably at least 400 milligrams of the pH-lowering agent are used in the pharmaceutical composition of the invention. The foregoing preferences relate to the total combined weight of all pH-lowering agents where two or more of such agents are used in combination. The oral formulation should not include an amount of any base which, when released together with the pH-lowering compound, would prevent the pH of the above-described sodium bicarbonate test from dropping to 5.5 or below.

The pH-lowering agent of the invention may be any pharmaceutically acceptable compound that is not toxic in the gastrointestinal tract and is capable of either delivering hydrogen ions (a traditional acid) or of inducing higher hydrogen ion content from the local environment. It may also be any combination of such compounds. It is preferred that at least one pH-lowering agent used in the invention have a pKa no higher than 4.2, and preferably no higher than 3.0. It is also preferred that the pH lowering agent have a solubility in water of at least 30 grams per 100 milliliters of water at room temperature.

Examples of compounds that induce higher hydrogen ion content include aluminum chloride and zinc chloride. Pharmaceutically acceptable traditional acids include, but are not limited to acid salts of amino acids (e.g. amino acid hydrochlorides) or derivatives thereof. Examples of these are acid salts of acetylglutamic acid, alanine, arginine, asparagine, aspartic acid, betaine, carnitine, carnosine, citrulline, creatine, glutamic acid, glycine, histidine, hydroxylysine, hydroxyproline, hypotaurine, isoleucine, leucine, lysine, methylhistidine, norleucine, ornithine, phenylalanine, proline, sarcosine, serine, taurine, threonine, tryptophan, tyrosine and valine.

Other examples of useful pH-lowering compounds include carboxylic acids such as acetylsalicylic, acetic, ascorbic, citric, fumaric, glucuronic, glutaric, glyceric, glycocolic, glyoxylic, isocitric, isovaleric, lactic, maleic, oxaloacetic, oxalosuccinic, propionic, pyruvic, succinic, tartaric, valeric, and the like.

Other useful pH-lowering agents that might not usually be called "acids" in the art, but which may nonetheless be useful in accordance with the invention are phosphate esters (e.g., fructose 1, 6 diphosphate, glucose 1, 6 diphosphate, phosphoglyceric acid, and diphosphoglyceric acid). CARBOPOL® (Trademark BF Goodrich) and polymers such as polycarbophil may also be used to lower pH.

Any combination of pH lowering agent that achieves the required pH level of no higher than 5.5 in the sodium bicarbonate test discussed above may be used. One preferred embodiment utilizes, as at least one of the pH-lowering agents of the pharmaceutical composition, an acid selected from the group consisting of citric acid, tartaric acid and an acid salt of an amino acid.

When salmon calcitonin is the peptide active agent, certain ratios of pH-lowering agent to salmon calcitonin have proven especially effective. It is preferred that the weight ratio of pH-lowering agent to salmon calcitonin exceed 200:1, preferably 800:1 and most preferably 2000:1.

The Absorption Enhancer

The absorption enhancers are preferably present in a quantity that constitutes from 0.1 to 20.0 percent by weight, relative to the overall weight of the pharmaceutical composition (exclusive of the enteric coating). Preferred absorption enhancers are surface active agents which act both as solubility enhancers and uptake enhancers. Generically speaking, "solubility enhancers" improve the ability of the components of the invention to be solubilized in either the aqueous environment into which they are originally released or into the lipophilic environment of the mucous layer lining the intestinal walls, or both. "Transport (uptake) enhancers" (which are frequently the same surface active agents used as solubility enhancers) are those which facilitate the ease by which peptide agents cross the intestinal wall.

One or more absorption enhancers may perform one function only (e.g., solubility), or one or more absorption enhancers may perform the other function only (e.g., uptake), within the scope of the invention. It is also possible to have a mixture of several compounds some of which provide improved solubility, some of which provide improved uptake and/or some of which perform both. Without intending to be bound by theory, it is believed that uptake enhancers may act by (1) increasing disorder of the hydrophobic region of the membrane exterior of intestinal cells, allowing for increased transcellular transport; or (2) leaching membrane proteins resulting in increased transcellular transport; or (3) widening pore radius between cells for increased paracellular transport.

Surface active agents are believed to be useful both as solubility enhancers and as uptake enhancers. For example, detergents are useful in (1) solubilizing all of the active components quickly into the aqueous environment where they are originally released, (2) enhancing lipophilicity of the components of the invention, especially the peptide active agent, aiding its passage into and through the intestinal mucus, (3) enhancing the ability of the normally polar peptide active agent to cross the epithelial barrier of the brush border membrane; and (4) increasing transcellular or paracellular transport as described above.

When surface active agents are used as the absorption enhancers, it is preferred that they be free flowing powders for facilitating the mixing and loading of capsules during the manufacturing process. Because of inherent characteristics of salmon calcitonin and other peptides (e.g., their isoelectric point, molecular weight, amino acid composition, etc.) certain surface active agents interact best with certain peptides. Indeed, some can undesireably interact with the charged portions of salmon calcitonin and prevent its absorption, thus undesireably resulting in decreased bioavailability. It is preferred, when trying to increase the bioavailability of salmon calcitonin or other peptides that any surface active agent used as an absorption enhancer be selected from the group consisting of (i) anionic surface active agents that are cholesterol derivatives (e.g., bile acids), (ii) cationic surface agents (e.g., acyl carnitines, phospholipids and the like), (iii) non-ionic surface active agents, and (iv) mixtures of anionic surface active agents (especially those having linear hydrocarbon regions) together with negative charge neutralizers. Negative charge neutralizers include but are not limited to acyl carnitines, cetyl pyridinium chloride, and the like. It is also preferred that the absorption enhancer be soluble at acid pH, particularly in the 3.0 to 5.0 range.

One especially preferred combination that has worked well with salmon calcitonin mixes cationic surface active agents with anionic surface active agents that are cholesterol derivatives, both of which are soluble at acid pH.

A particularly preferred combination is an acid soluble bile acid together with a cationic surface active agent. An acyl carnitine and sucrose ester is a good combination. When a particular absorption enhancer is used alone, it is preferred that it be a cationic surface active agent. Acyl carnitines (e.g., lauroyl carnitine), phospholipids and bile acids are particularly good absorption enhancers, especially acyl carnitine. Anionic surfactants that are cholesterol derivatives are also used in some embodiments. It is the intent of these preferences to avoid interactions with the peptide agent that interfere with absorption of peptide agent into the blood.

To reduce the likelihood of side effects, preferred detergents, when used as the absorption enhancers of the invention, are either biodegradable or reabsorbable (e.g. biologically recyclable compounds such as bile acids, phospholipids, and/or acyl carnitines), preferably biodegradable. Acylcarnitines are believed particularly useful in enhancing paracellular transport. When a bile acid (or another anionic detergent lacking linear hydrocarbons) is used in combination with a cationic detergent, salmon calcitonin is better transported both to and through the intestinal wall.

Preferred absorption enhancers include: (a) salicylates such as sodium salicylate, 3-methoxysalicylate, 5-methoxysalicylate and homovanilate; (b) bile acids such as taurocholic, tauorodeoxycholic, deoxycholic, cholic, glycholic, lithocholate, chenodeoxycholic, ursodeoxycholic, ursocholic, dehydrocholic, fusidic, etc.; (c) non-ionic surfactants such as polyoxyethylene ethers (e.g. Brij 36T, Brij 52, Brij 56, Brij 76, Brij 96, Texaphor A6, Texaphor A14, Texaphor A60 etc.), p-t-octyl phenol polyoxyethylenes (Triton X-45, Triton X-100, Triton X-114, Triton X-305 etc.) nonylphenoxypoloxyethylenes (e.g. Igepal CO series), polyoxyethylene sorbitan esters (e.g. Tween-20, Tween-80 etc.); (d) anionic surfactants such as dioctyl sodium sulfosuccinate; (e) lyso-phospholipids such as lysolecithin and lyso-phosphatidylethanolamine; (f) acylcarnitines, acylcholines and acyl amino acids such as lauroylcarnitine, myristoylcarnitine, palmitoylcarnitine, lauroylcholine, myristoylcholine, palmitoylcholine, hexadecyllysine, N-acylphenylalanine, N-acylglycine etc.; g) water soluble phospholipids such as diheptanoylphosphatidylcholine, dioctylphosphatidylcholine etc.; (h) medium-chain glycerides which are mixtures of mono-, di- and triglycerides containing medium-chain-length fatty acids (caprylic, capric and lauric acids); (i) ethylene-diaminetetraacetic acid; (j) cationic surfactants such as cetylpyridinium chloride; (k) fatty acid derivatives of polyethylene glycol such as Labrasol, Labrafac, etc.; and (l) alkylsaccharides such as lauryl maltoside, lauroyl sucrose, myristoyl sucrose, palmitoyl sucrose, etc.

In some preferred embodiments, and without intending to be bound by theory, cationic ion exchange agents (e.g. detergents) are included to provide solubility enhancement by another possible mechanism. In particular, they may prevent the binding of salmon calcitonin or other peptide active agents to mucus. Preferred cationic ion exchange agents include protamine chloride or any other polycation.

Other Optional Ingredients

It is preferred that a water-soluble barrier separate the pH-lowering agent from the acid resistant protective vehicle. In some of the examples which follow, a conventional pharmaceutical capsule is used for the purpose of providing this barrier. Many water soluble barriers are known in the art and include, but are not limited to, hydroxypropyl methylcellulose and conventional pharmaceutical gelatins.

In some preferred embodiments, another peptide (such as albumin, casein, soy protein, other animal or vegetable proteins and the like) is included to reduce non-specific adsorption (e.g., binding of peptide to the intestinal mucus barrier) thereby lowering the necessary concentration of the expensive peptide active agent. When added, the peptide is preferably from 1.0 to 10.0 percent by weight relative to the weight of the overall pharmaceutical composition (excluding protective vehicle). Preferably, this second peptide is not physiologically active and is most preferably a food peptide such as soy bean peptide or the like. Without intending to be bound by theory, this second peptide may also increase bioavailability by acting as a protease scavenger that desirably competes with the peptide active agent for protease interaction. The second peptide may also aid the active compound's passage through the liver.

All pharmaceutical compositions of the invention may optionally also include common pharmaceutical diluents, glycants, lubricants, gelatin capsules, preservatives, colorants and the like in their usual known sizes and amounts.

The Protective Vehicle

Any carrier or vehicle that protects the salmon calcitonin from stomach proteases and then dissolves so that the other ingredients of the invention may be released in the intestine is suitable. Many such enteric coatings are known in the art, and are useful in accordance with the invention. Examples include cellulose acetate phthalate, hydroxypropyl methylethylcellulose succinate, hydroxypropyl methylcellulose phthalate, carboxyl methylethylcellulose and methacrylic acid-methyl methacrylate copolymer. In some embodiments, the active peptide, absorption enhancers such as solubility and/or uptake enhancer(s), and pH-lowering compound(s), are included in a sufficiently viscous protective syrup to permit protected passage of the components of the invention through the stomach.

Suitable enteric coatings for protecting the peptide agent from stomach proteases may be applied, for example, to capsules after the remaining components of the invention have been loaded within the capsule. In other embodiments, enteric coating is coated on the outside of a tablet or coated on the outer surface of particles of active components which are then pressed into tablet form, or loaded into a capsule, which is itself preferably coated with an enteric coating.

It is very desirable that all components of the invention be released from the carrier or vehicle, and solubilized in the intestinal environment as simultaneously as possible. It is preferred that the vehicle or carrier release the active components in the small intestine where uptake enhancers that increase transcellular or paracellular transport are less likely to cause undesirable side effects than if the same uptake enhancers were later released in the colon. It is emphasized, however, that the present invention is believed effective in the colon as well as in the small intestine. Numerous vehicles or carriers, in addition to the ones discussed above, are known in the art. It is desirable (especially in optimizing how simultaneously the components of the invention are released) to keep the amount of enteric coating low. Preferably, the enteric coating adds no more than 30% to the weight of the remainder of pharmaceutical composition (the "remainder" being the pharmaceutical composition exclusive of enteric coating itself). More preferably, it adds less than 20%, especially from 12% to 20% to the weight of the uncoated composition. The enteric coating preferably should be sufficient to prevent breakdown of the pharmaceutical composition of the invention in 0.1N HCl for at least two hours, then capable of permitting complete release of all contents of the pharmaceutical composition within thirty minutes after pH is increased to 6.3 in a dissolution bath in which said composition is rotating at 100 revolutions per minute.

Other Preferences

It is preferred that the weight ratio of pH-lowering agent (s) to absorption enhancer(s) be between 3:1 and 20:1, preferably 4:1–12:1, and most preferably 5:1–10:1. The total weight of all pH-lowering agents and the total weight of all absorption enhancers in a given pharmaceutical composition is included in the foregoing preferred ratios. For example, if a pharmaceutical composition includes two pH-lowering agents and three absorption enhancers, the foregoing ratios will be computed on the total combined weight of both pH-lowering agents and the total combined weight of all three absorption enhancers.

It is preferred that the pH-lowering agent, the peptide active agent and the absorption enhancer (whether single compounds or a plurality of compounds in each category) be uniformly dispersed in the pharmaceutical composition. In one embodiment, the pharmaceutical composition comprises granules that include a pharmaceutical binder having the peptide active agent, the pH-lowering agent and the absorption enhancer uniformly dispersed within said binder. Preferred granules may also consist of an acid core, surrounded by a uniform layer of organic acid, a layer of enhancer and a layer of peptide that is surrounded by an outer layer of organic acid. Granules may be prepared from an aqueous mixture consisting of pharmaceutical binders such as polyvinyl pyrrolidone or hydroxypropyl methylcellulose, together with the pH-lowering agents, absorption enhancers and peptide active agents of the invention.

Manufacturing Process

A preferred pharmaceutical composition of the invention includes a size OO gelatin capsule filled with 0.25 mg. of salmon calcitonin, 400 mg. of granular citric acid (available for example from Archer Daniels Midland Corp.), 50 mg. of taurodeoxycholic acid (available for example from SIGMA), 50 mg. lauroyl carnitine (SIGMA).

All of the ingredients are preferably for eventual insertion into the gelatin capsule, and are preferably powders which may be added to a blender in any order. Thereafter, the blender is run for about five minutes until the powders are thoroughly intermixed. Then the mixed powders are loaded into the large end of the gelatine capsules. The other end of the capsule is then added, and the capsule snapped shut. 500 or more such capsules may be added to a coating device (e.g., Vector LDCS 20/30 Laboratory Development Coating System (available from Vector Corp., Marion, Iowa)).

An enteric coating solution is made as follows. Weigh 500 grams of EUDRAGIT L30 D-55 (a methacrylic acid copolymer with methacylic acid methyl ester, an enteric coating available from ROHM Tech Inc., Maidan, Mass.). Add 411 grams distilled water, 15 grams triethyl citrate and 38 grams talc. This amount of coating will be sufficient to coat about 500 size OO capsules.

The capsules are weighed and placed into the drum of the coating machine. The machine is turned on to rotate the drum (now containing capsules) at 24–28 rpm. The temperature of inlet sprayer is preferably about 45° C. Exhaust temperatures are preferably about 30° C. Uncoated capsule temperature is preferably about 25° C. Air flow is about 38 cubic feet per minute.

A tube from the machine is then inserted into the coating solution prepared as discussed above. The pump is then turned on for feeding solution into the coating device. Coating then proceeds automatically. The machine can be stopped at any time to weigh capsules to determine if the coating amount is sufficient. Usually coating is allowed to proceed for 60 minutes. The pump is then turned off for about five minutes while the machine is still running to help dry the coated capsules. The machine can then be turned off. The capsule coating is then complete, although it is recommended that the capsules be air dried for about two days.

Because of the enhanced bioavailability provided by the present invention, the concentration of expensive salmon calcitonin in the pharmaceutical preparation of the invention may be kept relatively low. Specific formulation examples are set forth in examples infra.

Treatment of Patients

When salmon calcitonin is chosen as active ingredient for treatment of osteoporosis, periodic administration is recommended. Salmon calcitonin is metabolized quickly with a half-life of only 20–40 minutes following subcutaneous administration in man. However, its beneficial effect on osteoclasts is much longer lasting, and may last for more than 24 hours notwithstanding rapid decrease in blood levels. There is usually no detectable blood levels more than two hours after injection of salmon calcitonin at conventional dosages. Accordingly, periodic administration of one dose about 5 days per week is preferred. Subcutaneous administration of salmon calcitonin (100 International units) has frequently resulted in peak serum concentration of about 250 picograms per milliliter. Nasally administered salmon calcitonin (200 International units) has proven effective against osteoporosis at peak levels as low as 10 picograms per milliliter. Some patients report some gastrointestinal distress at high peak levels (e.g. at or above 200 picograms per milliliter). Accordingly, it is preferred that serum salmon calcitonin peak between 10 and 150 picograms per milliliter, more preferably between 10 and 50 picograms per milliliter. The serum levels may be measured by radioimmunoassay techniques known in the art. The attending physician may monitor patient response, salmon calcitonin blood levels, or surrogate markers of bone disease (such as urinary pyridinoline or deoxypyridinoline), especially during the initial phase of treatment (1–6 months). He may then alter the dosage somewhat to account for individual patient metabolism and response.

The bioavailability achievable in accordance with the present invention permits oral delivery of salmon calcitonin into the blood at the above-identified preferred concentration levels while using only 100–1000 micrograms of salmon calcitonin per capsule, preferably 100–400 micrograms, especially between 100 and 200 micrograms.

It is preferred that a single capsule be used at each administration because a single capsule best provides simultaneous release of the polypeptide, pH-lowering agent and absorption enhancers. This is highly desirable because the acid is best able to reduce undesirable proteolytic attack on the polypeptide when the acid is released in close time proximity to release of the polypeptide. Near simultaneous release is best achieved by administering all components of the invention as a single pill or capsule. However, the invention also includes, for example, dividing the required amount of acid and enhancers among two or more capsules which may be administered together such that they together provide the necessary amount of all ingredients. "Pharmaceutical composition," as used herein includes a complete dosage appropriate to a particular administration to a human patient regardless of how it is subdivided so long as it is for substantially simultaneous administration.

Set forth below are a series of tables showing the effect on bioavailability caused by varying certain parameters. Except with regard to human studies reported here, ingredient amounts may be varied from those claimed herein to account for differences between humans and the animals used in the animal models.

TABLE 1

Effect of Buffer pH on the Absorption of
Salmon Calcitonin from the Duodenum of the Rat

| | Formulation | pH* | Peak Plasma Calcitonin ng/ml | Absolute Bioavailability percent |
|---|---|---|---|---|
| I. | Citrate/Citric acid (77 mg) Calcitonin (0.1 mg) | 5 | 0.4 | 0.02 |
| II. | Citrate/Citric acid (77 mg) Calcitonin (0.1 mg) | 4 | 1.9 | 0.10 |
| III. | Citrate/Citric acid (77 mg) Calcitonin (0.1 mg) | 3 | 4.1 | 0.64 |
| IV. | Citrate/Citric acid (77 mg) Calcitonin (0.1 mg) | 2 | 4.8 | 0.69 |

*buffer pH

Method:

Female Wistar rats (250–275 g) (n=3 for each formulation) were anesthetized with ketamine and xylazine prior to the insertion of a cannula in the carotid artery. The cannula was fitted to a three way valve through which blood was sampled and replaced with physiological saline. A midline incision was made in the abdominal cavity and 0.5 ml of formulation was injected directly into the exposed duodenum. The pH of the formulation was adjusted by mixing varying amounts of equal molar concentrations of citric acid and sodium citrate. Blood (0.5 ml) was collected before and at 5, 15, 30, 60 and 120 minutes after the administration of the formulation. Samples of blood were centrifuged for 10 minutes at 2600 g and the resulting plasma supernatant was stored as −20° C. The concentration of calcitonin in plasma was determined by a competitive radioimmunoassay. The absolute bioavailability (i.e., relative to an intravenous dose of calcitonin) was calculated from the areas under the curve obtained from plots of the plasma concentration of calcitonin as a function of time.

Results and Discussion:

When the pH of the buffer was reduced from 5 (formulation I) to 4 (formulation II) the absolute bioavailability increased 5 fold from 0.02% to 0.1%. When the pH was reduced to 3 (formulation III) the absolute bioavailability increased an additional 6.4 fold. There was very little increase in the bioavailability of calcitonin when the pH was reduced to 2. The overall bioavailability of calcitonin increased 32 fold when the pH of the buffer was reduced from 5 to 3.

TABLE 2

Effect of Citric Acid Concentration on the
Bioavailability of Salmon Calcitonin from the Duodenum of the Rat

| | Formulation | Peak Plasma Calcitonin ng/ml | Absolute Bioavailability percent |
|---|---|---|---|
| I. | Citric acid (9.6 mg) Taurodeoxycholic acid (5 mg) Mannitol (22 mg) Calcitonin (0.1 mg) | 3.65 | 0.25 |
| II. | Citric acid (48 mg) Taurodeoxycholic acid (5 mg) Mannitol (22 mg) Calcitonin (0.1 mg) | 17.44 | 2.43 |

Method:

Formulations consisting of a constant amount of taurodeoxycholic acid and 2 different amounts of citric acid in a total volume of 0.5 ml were administered into the duodenums of anesthetized rats as described in the legend to Table 1. Mannitol was included in formulations as a marker to measure paracellular transport. Samples of blood were removed at various times and analyzed for calcitonin as described previously.

Results and Discussion:

The bioavailability of salmon calcitonin administered in the presence of 9.6 mg citric acid (I) was 0.25%, whereas in the presence of 48 mg citric acid (II) the bioavailability was 2.43%. In the presence of a fixed amount of taurodeoxycholic acid the bioavailability of salmon calcitonin increased nearly 10 fold when the amount of citric acid in the formulation was increased only 5 fold.

TABLE 3

Effect of Enhancers in the Presence of Citric Acid on the
Absorption of Salmon Calcitonin from the Duodenum of the Rat

| | Formulation | Peak Plasma Calcitonin ng/ml | Absolute Bioavailability percent |
|---|---|---|---|
| I. | Citric acid (77 mg) Calcitonin (0.1 mg) | 4.8 | 0.69 |
| II. | Citric acid (48 mg) Taurodeoxycholic acid (5 mg) Calcitonin (0.1 mg) | 26.59 | 3.03 |
| III. | Citric acid (48 mg) Taurodeoxycholic acid (5 mg) Cetylpyridinium chloride (5 mg) Calcitonin (0.1 mg) | 36.48 | 4.54 |
| IV. | Citric acid (48 mg) Tween-20 (5 mg) Calcitonin (0.1 mg) | 15.50 | 3.10 |
| V. | Citric acid (48 mg) Sucrose ester-15 (5 mg) Mannitol (22 mg) Calcitonin (0.1 mg) | 38.93 | 5.83 |
| VI. | Citric acid (48 mg) Lauroylcarnitine chloride (5 mg) Calcitonin (0.1 mg) | 38.89 | 4.53 |
| VII. | Citric acid (48 mg) Diheptanoylphosphatidylcholine (5 mg) Calcitonin (0.1 mg) | 20.93 | 2.97 |

Method:

Formulations consisting of citric acid, calcitonin and various classes of enhancers in a total volume of 0.5 ml were administered into the duodenums of anesthetized rats as described in the legend to Table 1. Mannitol was included in formulation V as a marker to measure paracellular transport. Samples of blood were removed at various times and analyzed for calcitonin as described previously.

Results and Discussion:

In the absence of an enhancer, the absolute bioavailability of calcitonin was 0.69%. The inclusion of a water soluble phospholipid (formulation VII) increased the bioavailability 4.3 fold to 2.97%. The most effective enhancer was the sugar ester class (formulation V) in which the calcitonin bioavailability was 5.83%. The use of a mixture of bile acid and a cationic detergent (formulation III), a non-ionic detergent (formulation IV) and an acylcarnitine (formulation VI) resulted in intermediate bioavailabilities ranging from 3.03% to 4.53%. The differences in the bioavailabilities of calcitonin in the presence of various classes of enhancers are minor compared to that observed when only citric acid and no enhancer is present in the formulation.

TABLE 4

Effect of Lauroylcarnitine in the Presence of Various Additives on the Absorption of Salmon Calcitonin from the Duodenum of the Rat

| | Formulation | Peak Plasma Calcitonin ng/ml | Absolute Bioavailability percent |
|---|---|---|---|
| I. | Calcitonin (1 mg) | 9.44 | 0.096 |
| II. | Lauroylcarnitine chloride (5 mg) Calcitonin (0.1 mg) | 2.27 | 0.17 |
| III. | Lauroylcarnitine chloride (5 mg) Citric acid (48 mg) Calcitonin (0.1 mg) | 38.89 | 4.53 |
| IV. | Lauroylcarnitine chloride (1 mg) Citric acid (48 mg) Calcitonin (0.1 mg) | 27.72 | 4.81 |
| V. | Lauroylcarnitine chloride (5 mg) Diheptanoylphosphatidylcholine (5 mg) Citric acid (48 mg) Calcitonin (0.1 mg) | 44.89 | 6.45 |
| VI. | Lauroylcarnitine chloride (5 mg) Bovine Serum Albumin (25 mg) Calcitonin (0.1 mg) | 4.58 | 0.42 |

Method:

Formulations consisting of lauroylcarnitine, calcitonin and various other compounds in a total volume of 0.5 ml were administered into the duodenums of anesthetized rats as described in the legend to Table 1. Samples of blood were removed at various times and analyzed for calcitonin as described previously.

Results and Discussion:

In the absence of citric acid or any enhancer (formulation I), the absolute bioavailability of calcitonin was 0.096%. In the presence of 5 mg lauroylcarnitine chloride (formulation II), the bioavailability increased 1.8 fold to 0.17%. When citric acid was included with lauroylcarnitine (formulation III), the bioavailability increased an additional 27 fold to 4.53%. A 5 fold reduction in the amount of lauroylcarnitine but not citric acid (formulation IV), did not significantly reduce the bioavailability of salmon calcitonin. The inclusion of 5 mg diheptanoylphosphatidylcholine to formulation III to produce formulation V increased the bioavailability slightly (1.4 fold). The substitution of 25 mg bovine serum albumin for citric acid (formulation VI) reduced the bioavailability from 4.53% (formulation III) to 0.42%. These results taken together show the synergistic effect between a pH-lowering substance like citric acid and an enhancer like lauroylcarnitine.

TABLE 5

Effect of Formulation on the Absorption of Salmon Calcitonin from the Duodenum of the Dog

| | Formulation | Peak Plasma Calcitonin ng/ml | Absolute Bioavailability percent |
|---|---|---|---|
| I. | Calcitonin (25 mg) | 1.15 | 0.015 |
| II. | Citric acid (192 mg) Calcitonin (10 mg) | 10.65 | 0.37 |
| III. | Citric acid (192 mg) Taurodeoxycholic acid (20 mg) Calcitonin (5 mg) | 14.99 | 0.81 |

Method:

Modified vascular access ports were surgically implanted into the duodenum, ileum and colon of male beagle dogs. The septum/reservoir bodies of the ports were implanted under the skin and were used as sites for the administration of calcitonin formulations. Before and after the administration of calcitonin formulations into conscious dogs, the ports were flushed with 2 ml of the formulation without calcitonin. Blood (2 ml) was collected through angiocatheter tubes in the leg vein at t=30, 15 and 0 before administration of calcitonin and at 5, 10, 20, 30, 40, 50, 60 and every 15 minutes thereafter for 2 hours. Samples of blood were centrifuged for 10 minutes at 2600 g and the resulting plasma supernatant was stored at $-20°$ C. The concentration of calcitonin in plasma was determined by a competitive radioimmunoassay. The absolute bioavailability (i.e. relative to an intravenous dose of calcitonin) was calculated from the areas under the curve obtained from plots of the plasma concentration as a function of time obtained.

Results and Discussion:

The absolute bioavailability of calcitonin administered in water (I) was 0.015%. In the presence of 192 mg citric acid (II) the bioavailability of calcitonin increased 25 fold. The inclusion of 20 mg taurodeoxycholic acid in the formulation (III) produced an additional 2.2 fold increased in absolute bioavailability to 0.81%. The combination of a pH-lowering compound, citric acid, and an enhancer, taurodeoxycholic acid, resulted in overall 54 fold increased in the absolute bioavailability of salmon calcitonin.

TABLE 6

Effect of Dosage Form and Formulation on the Absolute Bioavailability of Salmon Calcitonin Administered Orally to Dogs

| | Capsule | Dissolution in HCl min | Formulation | Peak Plasma Calcitonin ng/ml | Peak Plasma Calcitonin min | Absolute Bioavailability percent |
|---|---|---|---|---|---|---|
| I. | Starch | 10 | Citric acid (100 mg) Taurodeoxycholic acid (100 mg) Calcitonin (10 mg) | 0.98 | 10–30 | 0.07 |

TABLE 6-continued

Effect of Dosage Form and Formulation on the
Absolute Bioavailability of Salmon
Calcitonin Administered Orally to Dogs

| Capsule | Dissolution in HCl min | Formulation | Peak Plasma Calcitonin ng/ml | Peak Plasma Calcitonin min | Absolute Bioavailability percent |
|---|---|---|---|---|---|
| II. Gelatin | 30 | Citric acid (100 mg) Taurodeoxycholic acid (100 mg) Calcitonin (10 mg) | 5.79 | 10–30 | 0.26 |
| III. Gelatin | 30 | Citric acid (600 mg) Taurodeoxycholic acid (80 mg) Calcitonin (5 mg) | 6.92 | 10–30 | 0.62 |
| IV. Gelatin | >60 | Citric acid (600 mg) Taurodeoxycholic acid (80 mg) Calcitonin (5 mg) | 7.79 | 90 | 1.48 |

Methods:

Starch and gelatin capsules were filled with the indicated formulations and coated for 60 min with either hydroxypropylmethylcellulose phthalate 50 (I,II,III)(1% weight gain) or Eudragit L 30 D-55 (IV)(10% weight gain) in a pan coater. The stability of the capsules in 0.1N HCl were determined in a dissolution bath using the "basket method." At least 2 dogs were given each of the indicated capsules by mouth and blood was sampled and analyzed for salmon calcitonin as previously described.

Results:

The bioavailability of 10 mg calcitonin mixed with 100 mg citric acid and 100 mg taurodeoxycholic acid and delivered in a starch capsule (I) was 0.07%. When the same formulation was given to dogs in a gelatin capsule (II), the bioavailability of salmon calcitonin increased to 0.26%. A six fold increase in the amount of citric acid and a 50% reduction in the amount of calcitonin (III) resulted in a nearly 3 fold increase in calcitonin bioavailability.

When the enteric coat was changed from hydroxypropylmethylcellulose phthalate 50 to Eudragit L 30 D-55, a methacrylate polymer and the formulation was kept the same (IV), the bioavailability of salmon calcitonin increased from 0.62% to 1.48%. Changing the enteric coat from hydroxypropylmethylcellulose phthalate 50 to Eudragit L 30 D-55 resulted in increased stability of the capsule in 0.1N HCl. This increased stability resulted in peak calcitonin levels appearing at a later time point in the dog's blood. The instability of capsules I, II and III in HCl suggests that these capsules were potentially opening in the dogs' stomachs, whereas the improved stability of capsule IV suggests that it was completely stable in the stomachs of dogs and was opening in the intestines of dogs. This indicates that a certain minimum enteric coating amount is preferred. At the same time, too much coating can delay release of calcitonin behind release of other important components (e.g., acid and detergent). Preferably, enteric coating adds 5 to 15% to the weight of the uncoated pharmaceutical.

TABLE 7

PHARMACOKINETICS OF ORAL CALCITONIN (10.5 mg) IN HUMANS

| Time min | Subject 1 | Subject 2 | Subject 3 | Subject 4 | Subject 5 | Mean |
|---|---|---|---|---|---|---|
| | | | Plasma Calcitonin (pg/ml) | | | |
| 0 | 0 | 0 | 0 | 0 | 0 | 0 |
| 15 | 34 | 0 | 0 | 0 | 1 | 7 |
| 30 | 497 | 91 | 206 | 0 | 70 | 173 |
| 40 | 327 | 86 | 99 | 26 | 35 | 114 |
| 50 | 173 | 114 | 78 | 117 | 26 | 102 |
| 60 | 87 | 106 | 40 | 180 | 20 | 87 |
| 70 | 72 | 108 | 64 | 63 | 35 | 68 |
| 80 | 27 | 85 | 54 | 30 | 25 | 44 |
| 90 | 43 | 102 | 46 | 19 | 14 | 45 |
| 100 | 40 | 89 | 28 | 17 | 28 | 41 |
| 110 | 0 | 91 | 16 | 13 | 0 | 24 |
| 120 | 49 | 117 | 34 | 0 | 6 | 41 |
| 180 | 34 | 107 | 0 | 0 | 16 | 31 |
| Bioavailability (%) | .06 | 0.04 | 0.03 | 0.02 | 0.02 | 0.03 |

Methods:

Starch capsules were filled with 138 mg citric acid, 105 mg taurodeoxycholic acid and 10.5 mg salmon calcitonin. The capsules were coated for 20 min with hydroxypropylmethylcellulose phthalate 50 in a pan coater and stored at 4° C. Fasted subjects were given 1 capsule followed by a glass of orange juice in the morning of the study. Samples of blood were taken 15 minutes before taking the capsules and at the indicated times after taking the calcitonin capsule. The concentration of calcitonin in blood was determined by competitive radioimmunoassay. The absolute bioavailability (i.e., relative to an intravenous dose of calcitonin) was calculated from the areas under curve obtained from plots of the plasma concentration of calcitonin as a function of time.

Results:

When 10 milligrams of salmon calcitonin alone was administered to humans, no detectable serum levels of salmon calcitonin resulted. However, when individuals were given the composition of the invention as described in Table 7, maximum levels of calcitonin were detected in the blood between 30 and 60 minutes after the individuals took the capsule. The maximum concentration of calcitonin in the blood was between 70 and 497 pg/ml. The mean peak concentration of calcitonin for the 5 individuals was 173 pg/ml at t=30 min. The absolute bioavailability ranged from 0.02 to 0.06% with a population mean of 0.03%.

TABLE 8

Effect of Citric Acid and Lauroylcarnitine on the
Bioavailability of Vasopressin, Calcitonin and Insulin In Rats

| Peptide | Formulation | Peak Plasma Peptide ng/ml | Absolute Bioavailability percent |
|---|---|---|---|
| [Arg$^8$]-Vasopressin | Vasopressin (1 mg) | 0.62 | 0.38 |
| | Vasopressin (0.1 mg) Citric Acid (48 mg) Lauroylcarnitine (5 mg) | 24.3 | 8.10 |
| Salmon Calcitonin | Calcitonin (1 mg) | 9.44 | 0.096 |
| | Calcitonin (0.1 mg) | 27.72 | 4.81 |

TABLE 8-continued

Effect of Citric Acid and Lauroylcarnitine on the
Bioavailability of Vasopressin, Calcitonin and Insulin In Rats

| Peptide | Formulation | Peak Plasma Peptide ng/ml | Absolute Bioavailability percent |
|---|---|---|---|
| | Citric Acid (48 mg) Lauroylcarnitine (5 mg) | | |
| Human Insulin | Insulin (1 mg) Citric Acid (48 mg) | 0.56 | 0.07 |
| | Insulin (1 mg) Citric Acid (48 mg) Lauroylcarnitine (5 mg) | 18.3 | 0.76 |

Method:

Formulations consisting of either [arg$^8$]-vasopressin, recombinant salmon calcitonin or human insulin and the indicated additives in a total volume of 0.5 ml were administered into the duodenums of anesthetized rats as described in the legend to Table 1. Samples of blood were removed at various times and analyzed for the indicated peptide as described previously.

Results and Discussion:

IN the absence of any additives the absolute bioavailability of intraduodenally administered [arg$^8$]-vasopressin was 0.38%. When citric acid and lauroylcarnitine were added to the formulation the bioavailability of vasopressin increased to 8.1%. The bioavailability of calcitonin in the absence of an acid and an enhancer was 0.096%, which was lower than that for unformulated vasopressin. However, when citric acid and lauroylcarnitine were included in the formulation, the absolute bioavailability increased 50 fold to 4.53%. In the absence of citric acid, human insulin could not even be dissolved in water. In the presence of citric acid all of the peptide was easily dissolved, and the absolute bioavailability of intraduodenally administered human insulin was 0.07%. The absolute bioavailability of insulin increased 10 fold when lauroylcarnitine was included in the formulation. These results indicate the bioavailability of unformulated peptides was at most 0.38% and that the inclusion of an organic acid, such as citric acid, and an enhancer, such as lauroylcarnitine, increased peptide bioavailability to as much as 8.1%

TABLE 9

PHARMACOKINETICS OF ORAL CALCITONIN (0.82 mg) IN HUMANS

| Time min | Subject 1 | Subject 2 | Subject 3 | Subject 4 | Subject 5 | Mean |
|---|---|---|---|---|---|---|
| | | | Plasma Calcitonin (pg/ml) | | | |
| 0 | 0 | 0 | 0 | 0 | 0 | 0 |
| 15 | 21 | 0 | 0 | 0 | 0 | 4 |
| 30 | 0 | 0 | 0 | 0 | 0 | 0 |
| 40 | 0 | 0 | 0 | 0 | 0 | 0 |
| 50 | 0 | 0 | 0 | 28 | 0 | 6 |
| 60 | 0 | 0 | 0 | 211 | 0 | 42 |
| 70 | 17 | 0 | 0 | 92 | 0 | 22 |
| 80 | 0 | 29 | 0 | 59 | 0 | 18 |
| 90 | 0 | 472 | 0 | | 623 | 274 |
| 100 | 48 | 199 | 151 | 27 | 210 | 127 |
| 110 | 17 | 75 | 71 | 23 | 108 | 59 |
| 120 | 598 | 33 | 69 | 20 | 53 | 155 |
| 180 | 25 | 0 | 0 | 0 | 0 | 5 |
| Bioavailability(%) | .52 | 0.14 | 0.16 | 0.41 | 0.68 | 0.38 |

Methods:

Gelatin capsules were filled with 473 mg citric acid, 75 mg taurodeoxycholic acid, 75 mg lauroylcarnitine and 0.82 mg salmon calcitonin. The capsules were coated for 60 min with Eudragit L30-D55 in pan coater and stored at 4° C. Fasted subjects were given 1 capsule followed by a glass of orange juice in the morning of the study. Samples of blood were taken 15 minutes before taking the capsules and at the indicated times after taking the calcitonin capsule. The concentration of calcitonin in blood was determined by competitive radioimmunoassay. The absolute bioavailability (i.e., relative to an intravenous dose of calcitonin) was calculated from the areas under curve obtained from plots of the plasma concentration of calcitonin as a function of time.

Results:

Maximum levels of calcitonin were detected in the blood between 50 and 180 minutes after the individuals took the capsule. The maximum concentration of calcitonin in the blood was between 211 and 623 pg/ml. The mean peak concentration ($C_{max}$) of calcitonin for the 5 individuals was 411 pg/ml which is approximately 5–10 times greater than the targeted therapeutic plasma level. The absolute bioavailability ranged from 0.14 to 0.68% with a population mean of 0.38%. These results indicated that even though the peptide content was reduced approximately 10 fold, the bioavailability of sCT compared to that obtained in Table 7 increased 10 fold by substituting gelatin capsules for starch capsules, by using Eudragit L30-D55 instead of hydroxymethylcellulose phthalate as the enteric coat, by increasing the amount of citric acid and by including lauroylcarnitine in the formulation.

Although the present invention has been described in relation to particular embodiments thereof, many other variations and modifications and other uses will become apparent to those skilled in the art. The present invention therefore is not limited by the specific disclosure herein, but only by the claims.

What is claimed is:

1. A pharmaceutical composition for oral delivery of a physiologically active peptide agent comprising:
   (A) a therapeutically effective amount of said active peptide;
   (B) at least one pharmaceutically acceptable pH-lowering agent;
   (C) at least one absorption enhancer effective to promote bioavailability of said active agent; and
   (D) an acid resistant protective vehicle effective to transport said pharmaceutical composition through the stomach of a patient while preventing contact between said active peptide agent and stomach proteases;
   wherein said pH-lowering agent is present in said pharmaceutical composition in a quantity which, if said composition were added to ten milliliters of 0.1M aqueous sodium bicarbonate solution, would be sufficient to lower the pH of said solution to no higher than 5.5.

2. The pharmaceutical composition of claim 1, wherein said pH-lowering compound is present in a quantity which, if said composition were added to ten milliliters of 0.1M aqueous sodium bicarbonate solution, would be sufficient to lower the pH of said solution to no higher than 3.5.

3. The pharmaceutical composition of claim 1, wherein said protective vehicle is present at a weight which is no more than 30% of the weight of the remainder of said pharmaceutical composition.

4. The pharmaceutical composition of claim 1, wherein said enteric coating is present at a weight which is no more than 20% of the weight of the remainder of said pharmaceutical composition.

5. The pharmaceutical composition of claim 1, wherein said enteric coating is present at a weight which is between 10% and 20% of the weight of the remainder of said pharmaceutical composition.

6. The pharmaceutical composition of claim 1, wherein said protective vehicle is sufficient to prevent breakdown of said pharmaceutical composition in 0.1N HCl for at least two hours, yet permits complete release of all contents of said pharmaceutical composition within thirty minutes after pH is increased to 6.3 in a dissolution bath in which said composition is rotating at 100 revolutions per minute.

7. The pharmaceutical composition of claim 1, wherein said absorption enhancer is a surface active agent.

8. The pharmaceutical composition of claim 7, wherein said surface active agent is absorbable or biodegradable.

9. The pharmaceutical composition of claim 8, wherein said surface active agent is selected from the group consisting of acylcarnitines, phospholipids and bile acids.

10. The pharmaceutical composition of claim 9, wherein said enhancer is an acyl carnitine.

11. The pharmaceutical composition of claim 10, further including a sucrose ester.

12. The pharmaceutical composition of claim 1, wherein said absorption enhancer is a surface active agent selected from the group consisting of (i) an anionic agent that is a cholesterol derivative, (ii) a mixture of a negative charge neutralizer and an anionic surface active agent, (iii) non-ionic surface active agents, and (iv) cationic surface active agents.

13. The pharmaceutical composition of claim 1, wherein said absorption enhancer is selected from the group consisting of a cationic surfactant and an anionic surfactant that is a cholesterol derivative.

14. The pharmaceutical composition of claim 1, wherein said pharmaceutical composition includes at least two absorption enhancers, one of which is a cationic surface active agent, and another of which is an anionic surface active agent that is a cholesterol derivative.

15. The pharmaceutical composition of claim 14, wherein said anionic surface active agent is an acid-soluble bile acid.

16. The pharmaceutical composition of claim 1, further comprising an amount of a second peptide that is not a physiologically active peptide effective to enhance bioavailability of said peptide active agent.

17. The pharmaceutical composition of claim 1, further comprising a water soluble barrier that separates said pH-lowering agent from said protective vehicle.

18. A pharmaceutical composition of claim 1, wherein said composition includes at least one pH-lowering agent that has a pKa no higher than 4.2.

19. The pharmaceutical composition of claim 1, wherein at least one pH-lowering agent has a solubility in water of at least 30 grams per 100 milliliters of water at room temperature.

20. The pharmaceutical composition of claim 1, wherein all ingredients other than said enteric coating are uniformly dispersed.

21. The pharmaceutical composition of claim 20, wherein said pharmaceutical composition comprises granules containing a pharmaceutical binder and, uniformly dispersed in said binder, said pH-lowering agent, said absorption enhancer and said peptide active agent.

22. The pharmaceutical composition of claim 1, wherein said composition is a solid dosage form wherein a weight ratio of said pH-lowering agent to said absorption enhancer is between 3:1 and 20:1.

23. The pharmaceutical composition of claim 1, wherein said composition is a solid dosage form wherein the weight ratio of said pH-lowering agent to said absorption enhancer is between 5:1 and 10:1.

24. The pharmaceutical composition of claim 1, wherein said pH-lowering agent is selected from the group consisting of citric acid, tartaric acid and an acid salt of an amino acid.

25. The pharmaceutical composition of claim 1, wherein said pH-lowering agent is present in an amount not less than 300 milligrams.

26. The pharmaceutical composition of claim 25, wherein said pH-lowering agent is present in an amount which is not less than 400 milligrams.

27. The pharmaceutical composition of claim 1, wherein said peptide agent is vasopressin.

28. The pharmaceutical composition of claim 1, wherein said peptide agent is salmon calcitonin.

29. The pharmaceutical composition of claim 1, wherein said peptide agent is insulin.

30. The pharmaceutical composition of claim 1, wherein said protective vehicle is a viscous protective syrup.

31. The pharmaceutical composition of claim 1, wherein said composition is for oral delivery of salmon calcitonin and comprises:
(A) a therapeutically effective amount of said salmon calcitonin;
(B) at least one pharmaceutically acceptable pH-lowering agent;
(C) at least one absorption enhancer effective to promote bioavailability of said salmon calcitonin; and
(D) an enteric coating;
wherein said pH-lowering agent is present in said pharmaceutical composition in a quantity which, if added to ten milliliters of 0.1M aqueous sodium bicarbonate solution, would be sufficient to lower the pH of said solution to no higher than 5.5.

32. The pharmaceutical composition of claim 31, wherein the weight ratio of said pH-lowering agent to said salmon calcitonin is at least 200:1.

33. The pharmaceutical composition of claim 31, wherein the weight ratio of said pH-lowering agent to said salmon calcitonin is at least 800:1.

34. The pharmaceutical composition of claim 31, wherein the weight ratio of said pH-lowering agent to said salmon calcitonin is at least 2000:1.

35. The pharmaceutical composition of claim 31, wherein at least one pH-lowering agent has a pKa not greater than 4.2 and a solubility in water of at least 30 grams per 100 milliliters of water at room temperature.

36. The pharmaceutical composition of claim 31, wherein a water soluble barrier separates said pH-lowering agent from said enteric coating.

37. The pharmaceutical composition of claim 31, wherein said salmon calcitonin, said pH-lowering agent and said absorption enhancer are uniformly dispersed.

38. The pharmaceutical composition of claim 28, wherein said enteric coating is present at a weight which is no more than 30% of the weight of the remainder of said pharmaceutical composition excluding said enteric coating.

39. The pharmaceutical composition of claim 1 for oral delivery of salmon calcitonin comprising:
(A) a therapeutically effective amount of said salmon calcitonin;
(B) at least one pharmaceutically acceptable pH-lowering agent having a pKa not higher than 4.2 and a solubility in water not lower than 30 grams per 100 milliliters of water at room temperature;
(C) at least one absorption enhancer effective to promote bioavailability of said salmon calcitonin;
(D) an enteric coating which is present at a weight which is between 10% and 20% of the weight of the remainder of said pharmaceutical composition; and
(E) a water-soluble barrier which separates said pH-lowering agent from said enteric coating;
wherein said pH-lowering agent is present in said pharmaceutical composition in a quantity which, if said pharmaceutical composition were added to 10 milliliters of 0.1M aqueous sodium bicarbonate solution, would be sufficient to lower the pH of said solution to no higher than 5.5; and
wherein said pharmaceutical composition comprises granules that include a pharmaceutical binder having said salmon calcitonin, said pH-lowering agent and said absorption enhancer uniformly dispersed therein.

40. The pharmaceutical composition of claim 1, wherein said peptide agent is calcitonin.

41. The pharmaceutical composition of claim 18, wherein said peptide agent is calcitonin.

42. The pharmaceutical composition of claim 22, wherein said peptide agent is calcitonin.

43. The pharmaceutical composition of claim 25, wherein said peptide agent is calcitonin.

44. A method for enhancing the bioavailability of a therapeutic peptide active agent delivered orally, said method comprising selectively releasing said peptide active agent, together with at least one pH-lowering agent and at least one absorption enhancer, into a patient's intestine following passage of said peptide active agent, pH-lowering agent and absorption enhancer through said patient's mouth and stomach under protection of an acid resistant protective vehicle which substantially prevents contact between stomach proteases and said peptide agent;
wherein said pH-lowering agent and other compounds released therewith are released into said intestine in a quantity which, if added to 10 milliliters of 0.1M aqueous sodium bicarbonate solution, would be sufficient to lower pH of said solution to no higher than 5.5.

45. The method of claim 44 wherein said pH-lowering compound is present in a quantity which, if all ingredients were added to 10 milliliters of 0.1M aqueous sodium bicarbonate solution, would be sufficient to lower the pH of said solution to no higher than 3.5.

46. The method of claim 44 wherein said protective vehicle is sufficient to prevent release of the other ingredients in 0.1M HCl for at least two hours, yet permits complete release of all ingredients within 30 minutes after pH is increased to 6.3 in a dissolution bath in which said protective vehicle and other ingredients are rotating at 100 revolutions per minute.

47. The method of claim 44 wherein said absorption enhancer is selected from the group consisting of a cationic surfactant and an anionic surfactant that is a cholesterol derivative.

48. The method of claim 44 wherein said pH-lowering agent has a pKa no higher than 4.2 and a solubility in water of at least 30 grams per 100 milliliters of water at room temperature.

49. The method of claim 44 wherein a weight ratio of said pH-lowering agent to said absorption enhancer is between 3:1 and 20:1.

50. The method of claim 44 wherein said pH-lowering agent is present in an amount of not less than 300 milligrams.

51. The method of claim 44, wherein said peptide agent is calcitonin.

52. The method of claim 44 wherein said peptide agent is salmon calcitonin.

53. The method of claim 52 wherein the weight ratio of said pH-lowering agent to said salmon calcitonin is at least 800:1.

54. The method of claim 52 wherein the weight ratio of said pH-lowering agent to said salmon calcitonin is at least 200:1.

55. The method of claim 52 wherein the weight ratio of said pH-lowering agent to said salmon calcitonin is at least 2000:1.

* * * * *